United States Patent [19]

Lempert et al.

[11] 4,432,901

[45] Feb. 21, 1984

[54] BETA-LACTAM COMPOUNDS CONTAINING A C-ACETAL GROUP AND PROCESS FOR THEIR PREPARATION

[75] Inventors: Karoly Lempert; Kalman Harsanyi; Gabor Doleschall; Gyula Hornyak; Jozsef Nitrai, all of Budapest; Karoly Zauer, Szentendre; Jozsef Fetter, Budapest; Gyula Simig, Budapest; Zsuzsanna Visky nee Gombos, Budapest; Gizella Barta nee Szalai, Vecses, all of Hungary

[73] Assignee: Richter Gedeon Vegyeszeti Gyar Rt., Budapest, Hungary

[21] Appl. No.: 301,884

[22] Filed: Sep. 11, 1981

[30] Foreign Application Priority Data

Sep. 15, 1980 [HU] Hungary ............................ 2262/80

[51] Int. Cl.³ .......................................... C07D 205/08
[52] U.S. Cl. ......................... 260/239 A; 260/245.2 T; 548/533; 562/568
[58] Field of Search .................................. 260/239 A

[56] References Cited

PUBLICATIONS

Shiozaki et al., Tetrahedron Letters 21, 4473 (1980).
Sankyo, Chem. Abs. 94, 103147y (1980).

*Primary Examiner*—Mark L. Berch
*Attorney, Agent, or Firm*—Karl F. Ross; Herbert Dubno

[57] ABSTRACT

The invention relates to new heterocyclic compounds containing a C-acetyl group and a process for their preparation. More particularly, the invention concerns new compounds of the formula (III).

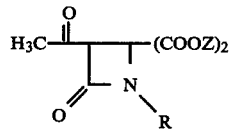

in which R is a protecting group suitable for temporary protection of amines and amides or an aryl group, and Z is alkyl.

The compounds are intermediates in the preparation of penicillins.

4 Claims, No Drawings

BETA-LACTAM COMPOUNDS CONTAINING A C-ACETAL GROUP AND PROCESS FOR THEIR PREPARATION

The invention relates to new heterocyclic compounds containing a C-acetyl group and a process for their preparation. More particularly, the invention concerns new compounds of the formula (III)

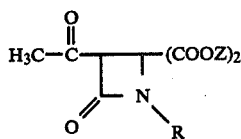

in which
R is a protecting group suitable for temporary protection of amines and amides or an aryl group, and
Z is alkyl.

In the definition of R the protecting group suitable for a temporary protection of amines and amides preferably is an optionally substituted benzyl group, and the term "aryl group" preferably is phenyl, which may optionally be substituted.

In the definition of Z the term "alkyl" is used to refer to straight or branched chain alkyl groups, preferably having 1 to 4 carbon atoms, more preferably methyl or ethyl.

The compounds of the formula (III), in which R represents a protecting group are valuable intermediates in new synthesis route for the preparation of thienamycin. The thienanycin synthesis in which the intermediates of the formula (III) are involved is illustrated on the Chart attached hereto. The most preferred representatives of the compounds of the formula (III) contain a 2,4-dimethoxybenzyl group in place of R.

Thienamycin is a well known antibiotic with a wide spectrum of activity, which has first been prepared microbiologically (U.S. Pat. No. 3,950,357) and then synthetically (Published German Patent Application No. 2,751,597).

Our intention was to provide a new synthesis route by which the azetidinone skeleton and the α-hydroxyethyl side chain (or another side chain, which can be easily converted into α-hydroxyethyl) can be formed simultaneously.

It has been found that by acylating a dialkyl (substituted amino)-malonate of the formula (I)

R—NH—CH(COOZ)$_2$     (I)

wherein R and Z are as defined hereinabove, with diketene and subjecting the acylated product to cyclization, directly the corresponding α-acetyl-(N-substituted)-acetidinone derivatives of the formula (III) are obtained, which can easily be converted into the desired (α-hydroxyethyl)-azetidinone derivatives.

According to another aspect of the invention there is provided a process for the preparation of new compounds of the formula (III), by reacting a compound of the formula (I), with diketene, and treating the compound of the formula (IIa)

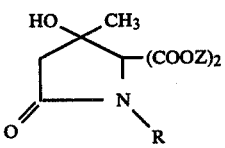

obtained, the reaction system of which optionally contains also a compound of the formula (IIb)

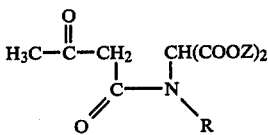

wherein R and Z are as defined above, with an alkali metal alcoholate and iodine or with a similar reactant, and isolating the compound of the formula (III) from the reaction mixture.

According to the invention in a first step of the synthesis of the compounds of the formula (III) a diethyl (substituted amino)-malonate of the formula (I) is acylated with diketene.

If compounds of the formula (III), suitable for the preparation of thienamycin are to be prepared, in the formula (I) R represents a protecting group suitable for a temporary protection of amino and amido groups, preferably benzyl or substituted benzyl, more preferably 4-methoxy-, 3,4-dimethoxy- or 2,4-dimethoxy-benzyl. The most preferred starting compound of the formula (I) is diethyl-(2,4-dimethoxybenzyl-amino)-malonate. The preparation of this new compound is disclosed in Example 1. The compound of the formula (I), in which R is benzyl is known in the art [P.J.Li: J.Org. Chem. 40 (23) 3414 (1975)].

If compounds of the formula (III) showing pharmaceutical activity are to be prepared, in the formula (I) R represents an aryl group, preferably a phenyl or chlorophenyl group. Some of the compounds of the formula (I), in which R stands for an aryl group, including the compounds, in which R is phenyl, are known in the art [Ber. 31 1815 (1895)]. The other representatives of the starting compounds of the formula (I) can be prepared by literature known processes.

The compounds of the formula (I) are reacted with diketene in the presence of an organic solvent. As an organic solvent an inert solvent, such as tetrahydrofurane and dioxane, or saturated aliphatic carboxylic acids, which are liquid at room temperature, e.g. formic acid, acetic acid, propionic acid, can be employed.

The reaction is preferably performed at elevated temperature, in certain cases at the boiling temperature of the solvent.

In the first reaction step compounds of the formula (IIa) and optionally (IIb) are obtained. In the concrete examples disclosed in the present application under the conditions of $^1$H-NMR (CDCl$_3$) measurement the form corresponding to the formula (IIa) could be detected. If a compound in which R is 2,4-dimethoxy-benzyl is prepared, also the tautomeric form corresponding to the formula (IIb) can be detected in the reaction mixture in an amount less than 5%. All the compounds of the formulae (IIa) and (IIb) are new.

In the second step of the reaction the compounds of the formula (IIa), which may contain also compounds of the formula (IIb), are converted into compounds of the formula (III). In this reaction step as a reactant alkali metal alcoholates and iodine or similar reactants are used. The reaction is preferably performed in the presence of an excess amount of the alkali metal alcoholate employed, preferably sodium or potassium ethylate or methylate. Iodine can be replaced by bromine or a combination of bromine and an alkali metal rhodanide. The most preferred reactants are iodine and sodium ethylate. The reaction is preferably accomplished in the presence of a lower alkanol, preferably ethanol, or a mixture of an alkanol and ether, under cooling.

The new compounds of the formula (III) obtained in the reaction are isolated from the reaction mixture by methods known in the art. The isolation can for example be carried out by thin layer chromatography or by extraction and/or evaporation.

Further details of the invention are illustrated by the following, non-limiting Examples.

EXAMPLE 1

(a) 50 g. (0.30 moles) of 2,4-dimethoxybenzaldehyde and 34.4 ml. (33.6 g., 0.31 moles) of benzyl amine in 300 ml. of dry toluene, in the presence of 1 g. of p-toluenesulfonic acid are boiled for 8 hours, while the water formed is continuously eliminated by a water separator. Thereafter toluene is distilled off. The residual oil is dissolved in 120 ml. of dioxane and 3.2 g. of sodium tetrahydroborate (III) are added with external ice cooling, followed by the addition of a further 3.2 g. portion of the same compound after stirring for two hours.

The reaction mixture is allowed to stand for 3 days, diluted with 400 ml. of water and the residual oil is shaken with ether, dried over magnesium sulfate, filtered and the filtrate is evaporated into half of its original volume. Thereafter hydrochloric acid in ethanol is added to the ethereal solution, dropwise, under cooling with ice water.

59 g. (67%) of benzyl (2,4-dimethoxybenzyl)amine hydrochloride are obtained, melting at 156° to 157° C. after crystallization from ethyl acetate.

Analysis for $C_{16}H_{20}ClNO_2$ (293.78): calculated: C 65.41%, H 6.86%, Cl 12.07%, N 4.77%, found: C 65.63%, H 7.30%, Cl 11.69%, N 4.72%.

(b) The compound obtained in the step (Ia), is converted into the corresponding base and 175 g. (0.68 moles) of benzyl (2,4-dimethoxy)-amine obtained are stirred with 89.6 g. (0.38 moles, 64 ml.) of diethyl bromomalonate at room temperature until the reaction mixture solidifies. The solidified mixture is triturated with about one lit. of ether and the crystalline precipitate is filtered off. (In this way the excess of the starting amine can be regained as hydrobromide with a yield of 95%). The filtrate is evaporated and the residual oil is triturated with ethanol. 114.5 g. (81%) of diethyl (N-benzyl-N-(2,4-dimethoxybenzyl)-amino-malonate are obtained, melting at 62° to 63° C. after crystallization from ethanol.

Analysis for $C_{23}H_{29}NO_6$ (415.47): calculated: C 66.49%, H 7.04%, N 3.37%; found: C 66.58%, H 7.09%, N 3.43%.

IR spectrum (KBr): 1750/1725 cm $^{-1}$, d.

(c) 61.7 g. (0.149 moles) of diethyl N-benzyl-N-(2,4-dimethoxybenzyl)-amino-malonate prepared according to Example (1b) are hydrogenated in the presence of about 20 g. of a palladium-on-charcoal catalyst, in 500 ml. of ethanol, under atmospheric pressure. 47.1 g. (97%) of diethyl (2,4-dimethocybenzylamino)-malonate are obtained, which if desired, can be converted into the corresponding hydrochloride with hydrochloric acid. The HCl salt melt at 122° to 124° C., after crystallization from ethyl acetate.

Analysis for $C_{16}H_{24}ClNO_6$ (361.82): calculated: C 53.11%, H 6.69%, Cl 9.80%, N 3.87%, found: C 52.51%, H 6.77%, Cl 10.30%, N 4.09%.

IR spectrum (film): 3250, 2900, 2850, 1730, 1720 cm $^{-1}$.

$^1$H-NMR spectrum (CDCl$_3$): 1.3 t (CH); 3.78 s (3H); 3.82 s (3H); 4.21 q (4H); 6.20 s (2H); 6.4–6.6 m (2H)+7.3–7.55 m (1H); 7.7 sz s (1H).

(d) 39.6 g. (0.122 moles) of diethyl (2,4-dimethoxybenzyl-amino)-malonate prepared according to Example (1c) are boiled with 12.3 g. (11.2 ml., 0.146 moles) of diketene in 80 ml. of glacial acetic acid for half an hour. The glacial acetic acid is distilled off on water bath, in vacuo, the residual oil is crystallized by trituration with 150 ml. of water, whereupon the substance is dissolved in 60 ml. of ethyl acetate and recrystallized by addition of petroleum ether. 29.6 g. (60%) of diethyl N-(2,4-dimethoxybenzyl)-3-hydroxy-3-methyl-5-oxo-2,2-pyrrolidine-dicarboxylate and/or the tautomer thereof are obtained. Melting point: 106° to 107° C.

Analysis for $C_{20}H_{27}NO_8$ (409.43): calculated: C 58.67%, H 6.65%, N 3.42%; found: C 58.79%, H 6.33%, N 3.34%.

IR spectrum (KBr): 3400, 2950, 2850, 1730 (1740 v), 1710 cm$^{-1}$.

$^1$H-NMR spectrum (CDCl$_3$): 1.1 t (3H); 1.17 t (3H); 1.52 s (~3H); 2.08 (<0.1H); 2.65 sz s (2H); 3.75 s (6H); 3.8–4.15 m (4H); 6.7 sz s (2H); 6.25–6.45 m+7.0–7.25 m (3H).

(e) 20.5 g. (50 mmoles) of the product of Example (1d) are suspended in 50 ml. of dry ether and by two dopping funnels, simultaneously 3.45 g. (150 mmoles) of sodium metal in 100 ml. of dry ethanol and 12.7 g. (50 mmoles) of iodine in 150 ml. of dry ether are rapidly added under vigorous stirring, with external ice cooling. To the mixture 5. g. sodium hydrogensulfite dissolved in 200 ml. saturated aqueous sodium chloride solution are added. The mixture is poured into a separating funnel and the precipitation of inorganic salts is stopped by adding 60 ml. of water. The aqueous phase is separated and shaken with two 100-ml. portions of ether. The organic phase is dehydrated with magnesium sulfate, filtered and the filtrate is evaporated. The oily residue (18.5 g.) is recrystallized from 30 ml. of 2-propanol. 10.9 g. (54%) of diethyl 3-acetyl-1-(2,4-dimethoxybenzyl)-4-oxo-2,2-azetidine-dicarboxylate are obtained, melting at 84° to 85° C. after recrystallization from 2-propanol.

Analysis for $C_{20}H_{25}NO_8$ (407.41): calculated: C 58.96%, H 6.19%, N 3.44%; found: C 58.99%, H 6.04%, N 3.57%.

IR spectrum (KBr): 2900, 1780, 1740, 1710 cm$^{-1}$.

$^1$H-NMR spectrum (CDCl$_3$): δ1.12 t (3H); 1.21 t (3H); 2.31 s (3H); 3.76 s (6H); 3.8–4.2 m (4H); 4.53 d (1H); 4.63 d (1H); 4.69 s (1H); 6.3–6.4 m (2H)+7.07 d (1H).

EXAMPLE 2

(a) To a mixture of 59.2 g. (41.2 ml., 0.199 moles) of diethyl bromomalonate and 22.5 g. (31.5 ml., 0.225 moles) of triethyl amine 24 g. (24.3 ml., 0.207 moles) of benzyl amine are added dropwise, under intensive external cooling with ice water, with vigorous stirring. A thick mixture is obtained, which is difficult to stir. The mixture is allowed to stand for 1.5 hours, triturated with 100 ml. of ether, the precipitated crystals are filtered off and to the filtrate hydrochloric acid in ethanol is added dropwise. The crystalline precipitate is filtered off and washed with ether.

23 g. (31%) of diethyl benzylamino-malonate. HCl (compound of the formula (I) are obtained, melting at 146° to 148° C., with decomposition.

(b) 2.52 g. (9.5 mmoles) of diethyl benzylamino-malonate prepared according to Example (2a) in 10 ml. of glacial acetic acid are stirred with 0.8 g. (0.73 ml., 9.5 mmoles) of diketene. The glacial acetic acid is distilled off in vacuo. 3.06 g. (92%) of diethyl N-benzyl-3-hydroxy-3-methyl-5-oxo-2,2-pyrrolidine-dicarboxylate of the formula (IIa) and/or the tautomer having the formula (IIb) thereof (N-acetoacetyl-N-benzylamino malonate) are obtained as an oily product.

IR spectrum (film): 3350, 2950, 1750-1670 cm$^{-1}$.

$^1$H-NMR spectrum (CDCl$_3$): 1.12 t (6H); 1.51 (3H); 2.68 s (2H); 3.65-4.25 m (5H); 4.8 s (2H); 7.2 s (5H).

(c) The product of Example (2b) is reacted with sodium ethylate and iodine as described in Example (1c). by preparative thin layer chromatography diethyl 3-acetyl-1-benzyl-4-oxo-2,2-azetidine-dicarboxylate is isolated as an oily product. (Kieselgel-60, PF$_{254+366}$, 7093 mixture of benzene and acetone.

IR spectrum (film): 2900, 1770-1700 cm$^{-1}$.

$^1$H-NMR spectrum (CDCl$_3$): 1.08 t (3H); 1.22 t (3H); 2.3 s (3H); 3.7-4.3 m (4H); 4.5 d (1H); 4.8 s (1H); 7.28 s (5H).

$^{13}$C-NMR spectrum (CDCl$_3$): 13.61; 13.75; 30.07; 46.12; 62.47; 62.68; 65.74; 68.67; 127.74; 128.20; 128.37; 128.46; 128.64; 135.53; 162.57; 166.18; 166.30; 197.42.

EXAMPLE 3

(a) 38 g. (0.152 moles) of diethyl anilino-malonate [R. Blank: Ber. 31, 1815 (1898)] are boiled in 38 ml. of glacial acetic acid with 15.3 g. (13.9 ml., 0.182 moles) of diketene for half an hour. The glacial acetic acid is distilled off in vacuo, on water bath. The residual oil is crystallized by trituration with ether.

36.5 g. (72%) of diethyl N-phenyl-3-hydroxy-3-methyl-5-oxo-2,2-pyrrolidine-dicarboxylate of the formula (IIa) and/or a corresponding compound of the formula (IIb) is obtained. Melting point: 98° to 99° C. (a mixture of ethyl acetate and petroleum ether).

Analysis for C$_{17}$H$_{21}$NO$_6$ (335.35): calculated: C 60.88%, H 6.31%, N 4.18%; found: C 60.83%, H 6.15%, N 4.43%.

IR spectrum (KBr): 3350, 2950, 1760+1750 d, 1700 cm$^{-1}$.

$^1$H-NMR spectrum (CDCl$_3$): 1.02 t (3H); 1.3 t (3H); 1.6 s (3H); 2.8 s (2H); 3.6 sz s (1H); 4-4.45 m (4H); 7.2 s (5H).

(b) 10.2 g. (0.447 moles) of sodium metal are dissolved in 250 ml. of dry ethanol and 50 g. (0.149 moles) of diethyl N-phneyl-3-hydroxy-3-methyl-5-oxo-2,2-pyrrolidine-dicarboxylate prepared according to the Example (3a) are added to the solution, followed by the addition of 37.9 g. (0.149 moles) of iodine in 200 ml. of dry ether, under vigorous stirring. When the reaction is complete, 8.5 ml. (89 g., 0.149 moles) of glacial acetic acid, 200 ml. of water and 100 ml. of ether are added to the reaction mixture, the organic phase is separated and the aqueous phase is shaken with 100 ml. of ether. The ethereal phases are combined, dried with magnesium sulfate, filtered and the filtrate is evaporated. The oily residue is recrystallized from 50 ml. of 2-propanol. 31 g. (62%) of diethyl 3-acetyl-1-phenyl-4-oxo-2,2-azetidine-dicarboxylate of the formula (III) are obtained, melting at 55° to 56° C.after crystallization from 2-propanol.

Analysis for C$_{17}$H$_{19}$NO$_6$: calculated: C 61.25%, H 5.75%, N 4.20%, found: C 61.38%, H 5.89%, N 4.24%.

IR spectrum (KBr): 1770, 1740, 1720 cm$^{-1}$.

$^1$H-NMR spectrum (CDCl$_3$): 1.12 t (6H); 2.3 s (3H); 4.25 q (4H); 4.75 s (1H); 7.0-7.6 m (5H).

EXAMPLE 4

The reaction steps disclosed in Examples (1a) and (1b) can be performed also in a combined version, without isolating the product of Example (1a), as follows:

109.7 g. (0.66 moles) of 2,4-dimethoxy-benzaldehyde and 72 ml. (0.66 moles) of benzyl amine in 660 ml. of methanol are stirred at room temeprature for 20 minutes. The initial suspension slowly turns to a clear solution. To this solution 13.3 g. (0.33 moles) of sodium tetrahydroborate (III) are added in small portions, under outer cooling with ice water.

The progress of the reaction is monitored by thin layer chromatography (Kieselgel G according to Stahl, a 9:1 mixture of benzene and acetone). When the reaction is complete, the mixture is evaporated to dryness in vacuo, to the residue 300 ml. of water are added and it is shaken with 500 ml. of ether. The aqueous phase is extracted with two 200 ml. portions of ether. The combined ethereal phases are dried with magnesium sulfate, filtered, whereupon 112 ml. (0.66 moles) of diethyl bromomalonate and 93 ml. (0.66 moles) of triethyl amine are added to the ethereal solution. The reaction mixture is stirred at room temperature for 2 to 3 days. The precipitated triethylammonium bromide is filtered and washed with ether. The mother liquor is crystallized from 150 ml. of ethanol. 210 g. of a crude product are obtained, which is recrystallized from 400 ml. of ethanol.

197 g. (7@%) of diethyl N-benzyl-N-(2,4-dimethoxybenzyl)-amino-malonate are obtained. The physical constants of the product obtained are identical with those of the product of Example (1b).

The Text of Chart A 1 formation of ketal or thioketal (preferably with ethylene glycol or mercapto ethanol)
2 wherein Y$^1$+Y$^2$=ketal or thioketal
3 alkali metal halide
4 alkyl-or arylsulfonic acid halide
5 wherein R$^1$ is alkyl or aryl
6 wherein Q is alkyl, preferably methyl or ethyl
7 acetone
8 2, chloroformic acid p-nitro-benzylester
9 wherein R$^2$ is p-nitro-benzyloxycarbonyl
10 2,3-dihydropyrane or acetic anhydride
11 wherein R$^3$ is tetrahydropyranyl or acetyl
12 elimination of R and R$^3$

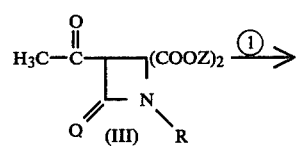

-continued

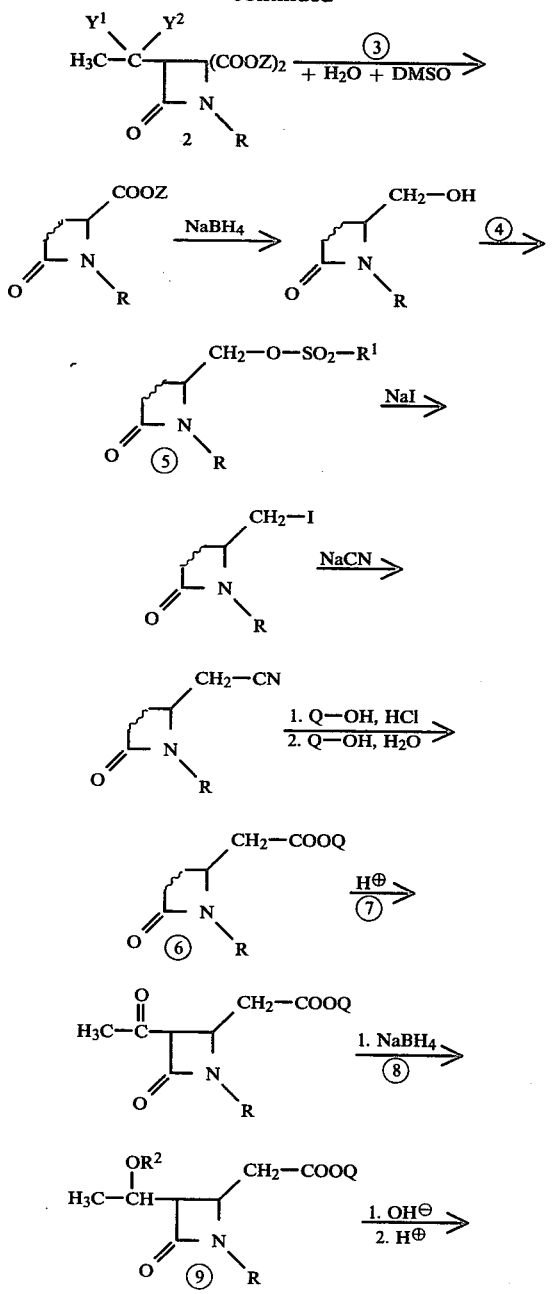

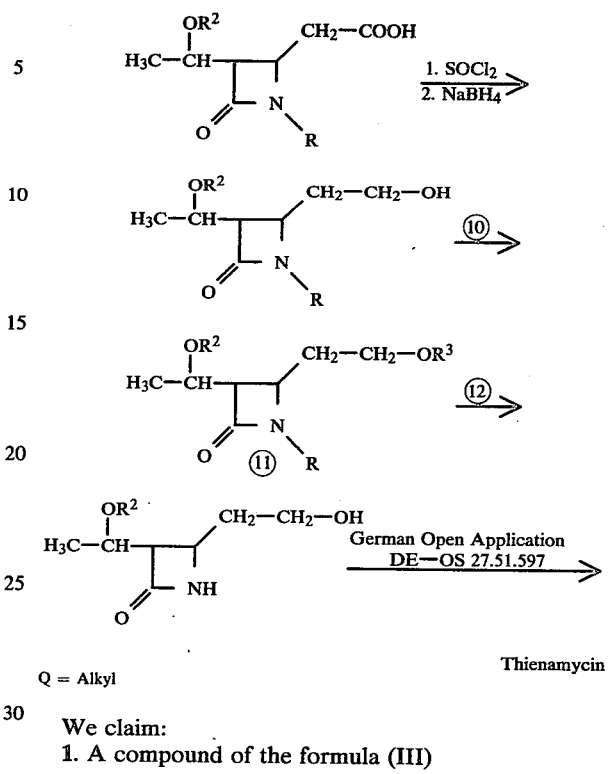

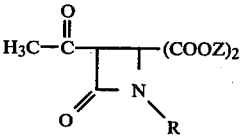

Q = Alkyl

Thienamycin

We claim:
1. A compound of the formula (III)

wherein
R is benzyl, 4-methoxy-benzyl, or 2,4-dimethoxy-benzyl; and
Z is $C_1$ to $C_4$ alkyl.
2. The compound defined in claim 1, in which R is 2,4-dimethoxy-benzyl and Z is methyl or ethyl.
3. The compound defined in claim 1 which is diethyl-3-acetyl-1-(2,4-dimethoxy-benzyl)-4-oxo-2,2-azetidine-dicarboxylate.
4. The compound defined in claim 1 which is diethyl 3-acetyl-1-benzyl-4-oxo-2,2-azetidine-dicarboxylate.

* * * * *